United States Patent [19]

Wondrazek et al.

[11] Patent Number: 4,932,954

[45] Date of Patent: Jun. 12, 1990

[54] APPARATUS FOR FRAGMENTATION OF A SOLID BODY SURROUNDED BY A FLUID

[75] Inventors: Fritz Wondrazek, Pfaffenhofen; Gisela Diepold, Germering, both of Fed. Rep. of Germany

[73] Assignee: Messerschmitt-Bölkow-Blohm GmbH, Munich, Fed. Rep. of Germany

[21] Appl. No.: 106,156

[22] Filed: Oct. 8, 1987

[30] Foreign Application Priority Data

Nov. 13, 1986 [DE] Fed. Rep. of Germany ....... 3638723

[51] Int. Cl.$^5$ ............................................. A61B 17/22
[52] U.S. Cl. ...................................... 606/128; 606/15
[58] Field of Search ................. 128/24 A, 24.1, 303.1, 128/328

[56] References Cited

U.S. PATENT DOCUMENTS

| | | | |
|---|---|---|---|
| 3,902,499 | 9/1975 | Shene | 128/328 |
| 4,207,874 | 6/1980 | Choy | 128/303.1 |
| 4,273,109 | 6/1981 | Enderby | 128/303.1 |
| 4,418,688 | 12/1983 | Loeb | 128/303.1 |
| 4,535,771 | 8/1985 | Takayama | 128/328 |
| 4,608,979 | 9/1986 | Breidenthal et al. | 128/303.1 |
| 4,676,231 | 6/1987 | Hisazumi et al. | 128/303.1 |
| 4,694,828 | 9/1987 | Eichenbaum | 128/303.1 |

FOREIGN PATENT DOCUMENTS

| | | | |
|---|---|---|---|
| 2538960 | 4/1977 | Fed. Rep. of Germany ... | 128/24 A |
| 3506249 | 8/1986 | Fed. Rep. of Germany ...... | 128/328 |
| 8606953 | 12/1986 | France ................................. | 128/328 |

OTHER PUBLICATIONS

Fair, Harry D., Jr., *In Vitro Destruction of Urinary Calculi . . .*, Med. Instr., vol. 12, No. 2, Mar.–Apr. 1978.

Primary Examiner—Kyle L. Howell
Assistant Examiner—John D. Zele
Attorney, Agent, or Firm—Kenyon & Kenyon

[57] ABSTRACT

An apparatus for the fragmentation of a solid body surrounded by a fluid, in particular in a living being, by means of acoustic shock waves which are induced by the light of a laser. A reflector for acoustic waves focuses the shock waves onto the body. In the region of the reflector, an element is provided which consists of a material absorbing the laser light, and onto which the laser light is directed, so that the plasma state triggering the acoustic shock wave develops at the surface of the element. The apparatus thus has the advantage that even under unfavorable conditions acoustic shock waves can be generated with certainty at every laser pulse.

11 Claims, 2 Drawing Sheets

APPARATUS FOR FRAGMENTATION OF A SOLID BODY SURROUNDED BY A FLUID

BACKGROUND OF THE INVENTION

The present invention relates to an apparatus for the fragmentation of a solid body surrounded by a fluid, in particular in a living being.

Such an apparatus is known from DE-OS 35 06 249. In this known apparatus, a laser beam is used having so great a power that in the focus point the "breakdown threshold" of the fluid is exceeded. "Breakdown" designates a strong ionization of a medium in the focus of a laser beam. The energy then transformed in the focal region increases approximately exponentially with time by cascade ionization, so that a hot plasma forms which expands abruptly and thereby induces an acoustic shock wave.

With this known apparatus, kidney stones, for example, can be destroyed similarly as in extracorporal shock wave, lithotripsy.

According to the invention, however, it has been found that the principle of forming shock waves in the body-specific fluid, as pursued with this apparatus, may under certain circumstances have disadvantages:

To bring about a breakdown in a fluid, e.g water, a radiation power of about $6.4 \times 10^{13}$ W/m2 is required, so that the laser beam must be focused on a comparatively small region.

In the fragmentation of kidney stones, a plurality of small and extremely small particles is formed, which inter alia may therefore enter the region of the laser beam. These particles or also already existing suspensoids, e.g. so-called kidney grit, can enter the region of the focused laser beam and absorb it, disperse it, etc., so that the "breakdown power" is not reached.

SUMMARY OF THE INVENTION

It is an object of the present invention to develop an apparatus such that even under unfavorable conditions, as for instance after several kidney stone fragmentations one after the other, shock waves can be generated with certainty at every laser pulse.

According to the invention, the laser beam is directed onto an element which consists of a material which linearly or nonlinear absorb the laser light energy. Thus, in the apparatus according to the invention, the formation of the plasma state, whose expansion triggers the shock wave, begins, not in the fluid, but at the surface of the element.

This results in a number of advantages:

Due to the use of the element, at which the shock wave "crystallizes", a much lesser energy density is necessary than in the known apparatus, where the shock wave is "crystallized" in the fluid. Thus, in contrast to the known apparatus, it is no longer necessary to focus the laser beam; instead, it suffices to "direct" the laser beam issuing, for example, from a light guide onto the element. Thus one can dispense with a focusing lens susceptible to contamination, which in the prior art may moreover often be destroyed by the plasma formation in the immediate vicinity or whose optical properties may change.

Moreover, this "directed" laser beam of comparatively large diameter is "disturbed", i.e. dispersed or absorbed, much less by small "suspensoids" such as fragments, kidney grit etc. than the beam focused on a small focal spot in the prior art.

It may furthermore be provided to supply, in the region of the element, a rinse fluid, for instance water or a medically compatible fluid (liquid or gas), which in the region of the element issues from the apparatus at least in part. The fluid flow caused thereby flushes fragments etc. of the body to be fragmented out of the region of the generated shock wave, so that subsequent shock waves are not damped. Also, the flow reliably prevents the deposition of fragments, suspensoids, etc. on the apparatus designed according to the invention.

According to a further embodiment, a suction means draws off in particular the rinse fluid and the fragments of the fragmented body. It is achieved thereby that a minimum of rinse fluid and a minimum of fragments remain in the living being.

The element at which the shock waves "crystallize" may consist of a variety of materials. It is, however, especially advantageous to use a metal, e.g. platinum, as the useful life of such a "crystallization element" is very long and only little material is evaporated by the laser beam. A "special steel" material may be used which advantageously combines resistance to corrosion, useful life and favorable costs.

Various forms of the element at which the shock wave forms are disclosed herein. The various designs each have specific advantages with respect to the shape of the resulting shock wave, the protection of the reflector and of the exit end of the light guide against fragments, as well as the efficiency of the transformation of the energy of the laser into shock wave energy, so that an appropriate element can be chosen depending on the practical case. It is then readily possible to design the apparatus so that a variety of element forms can be employed.

It is the function of the reflector, in known manner, to direct the resulting shock waves onto the body to be fragmented. The form of the reflector must be chosen accordingly. A preferred design of the reflector, where the focusing occurs with high efficiency, is described herein.

Preferred variants also are described which greatly facilitate the handling and clearly reduce the diameter of the apparatus.

BRIEF DESCRIPTION OF THE DRAWINGS

In the following, the invention will be described more specifically with reference to the drawings, in which.

DETAILED DESCRIPTION

Figure 1:
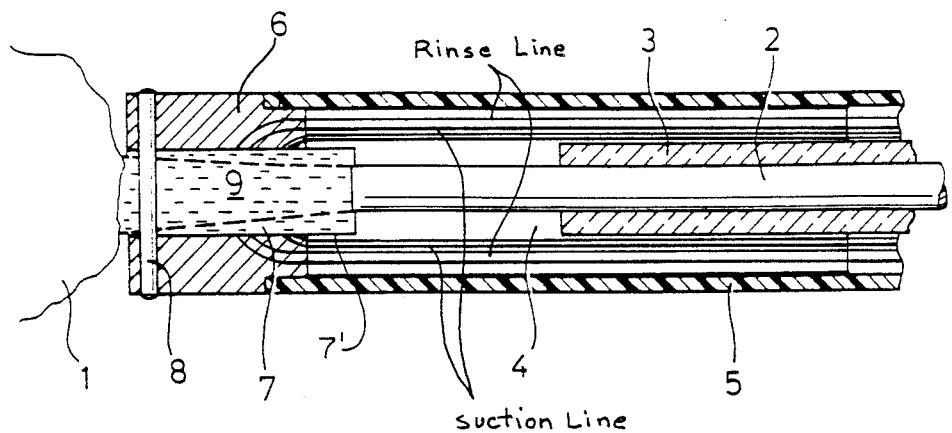
FIG. 1 shows a transverse section through an apparatus according to the invention.
Figure 2:
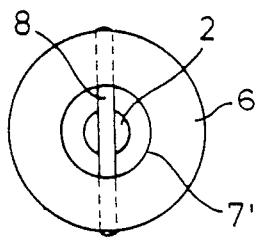
FIG. 2 shows a front view of the apparatus illustrated in FIG. 1.

The apparatus illustrated in the figures for the fragmentation of a body 1 surrounded by a fluid comprises a light guide 2 with a light guide sheath 3. At the exit-side end of the apparatus the light guide 2 is held by a spacer element 4 on which is fitted a plastic hose 5 which concentrically surrounds the light guide 2. Connected with the spacer element 4 is a holder 6 which has a cavity 7 in which a reflector 7' for acoustic waves is arranged or respectively which is designed as reflector, and in which the light guide 2 terminates. At the front (exit-side) end of the holder 6 an element 8 is fastened to holder 6, which element in the embodiment shown is a metal wire arranged at the focus of the reflector 7'.

The spacer element 4 is slit, so that a rinse medium 9, which flows through the interstice between light guide sheath 3 and plastic hose 5, can flow out into the cavity 7 in holder 6.

The apparatus described operates as follows:

The light of a laser issuing from the light guide 2 is directed (not focused) onto the metal wire 8 and creates a plasma state at the surface of the metal wire. The end of the holder 6 is placed closely adjacent the body 1 to be fragmented, as shown, although it need not be placed into actual contact with the body. The plasma expands and triggers, in a manner known per se, a shock wave which is focused by the reflector 7' onto the body 1 to be fragmented and fragments it. The fluid discharges fragments and any gases that may form as the laser impinges, so that the region of the shock wave remains largely free from fragments.

Figure 4:
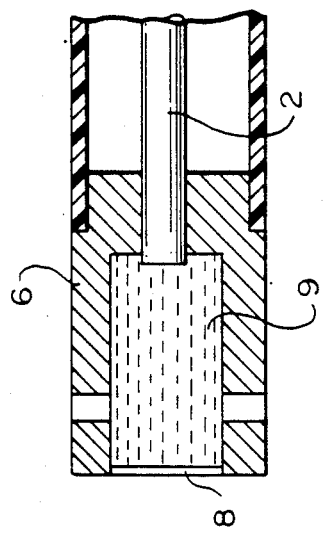
FIG. 4 shows the invention utilizing a metal foil element.
Figure 5:
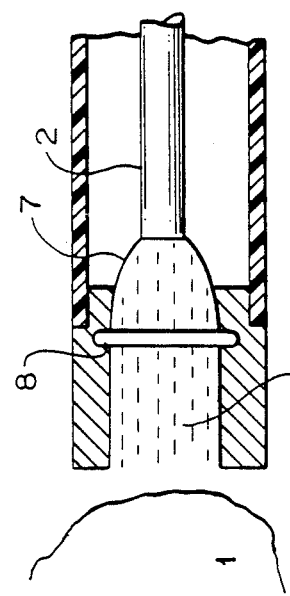
FIG. 5 shows the invention having an ellipsoidal reflector.

In the foregoing, the invention has been described with reference to an embodiment without restriction of the general inventive idea to provide an element at which the acoustic "plasma" shock waves form. Within this general inventive idea, of course, a variety of modifications are possible:

For example, the wire type element used in the embodiment illustrated can be replaced by other forms, e.g. grid or foil type element, as shown in FIG. (grid) and FIG. 4 (foil). In the latter case, as is apparent, suitable openings for the rinse fluid are provided in the holder 6. The element may also be disposed removably in the holder 6.

The reflector 7' may have the form of an elliptical element also a spherical reflector may be used.

Moreover it is possible also to provide a suction line, which in particular removes the supplied fluid and the resulting fragments. The discharge of the rinse fluid may alternatively occur at a different point, for example the rinse fluid may issue from an annular opening adjacent the element.

Then also it is conceivable to integrate the apparatus in an endoscope and/or to provide it with an image sensor, to be able to check the outcome of the treatment.

The element 8, which preferably is made of metal, may be made of e.g., platinum. A special steel, e.g., stainless steel, may also be used for long life, corrosion resistance and to keep costs down.

In the foregoing specification, the invention has been described with reference to an exemplary embodiment thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. Apparatus for the intracorporal fragmentation of a solid body surrounded by a fluid, in particular in a living being, by acoustic shock waves which are induced by the energy of a laser comprising a housing, laser energy guide means for transmitting laser energy to an open end of the housing, a reflector having a focus and being disposed in the housing and further being coupled to said laser energy guide means, the housing defining a holder for holding said reflector and said laser energy guide means attached to said reflector, said housing adapted to be inserted into a living being adjacent a solid body to be fragmented, acoustic shock waves induced by the laser energy being focused onto the body by said reflector thereby fragmenting as solid body, and further comprising an element provided in the region of the focus of the reflector which comprises a material which absorbs the laser energy, and onto which the laser energy is directed by the laser energy guide means, so that a plasma state triggering the acoustic shock wave develops at the surface of the element.

2. The apparatus recited in claim 1, further comprising a rinse fluid line disposed between said housing and said lower energy guide means for provide a rinse fluid to be issued at the end of said housing.

3. The apparatus recited in claim 2, wherein a suction means is provided for drawing off in particular the rinse fluid and the fragments of the fragmented body.

4. The apparatus recited in claim 2, wherein said holder retains said element, said laser energy guided means terminating in the holder, the element being inserted removably in the holder.

5. The apparatus recited in claim 2, further comprising a suction line provided surrounding the laser energy guide means for drawing off the rinse fluid and fragments of the solid body being fragmented.

6. The apparatus recited in claim 1, wherein the element comprises metal.

7. The apparatus recited in claim 6, wherein the element comprises a stainless steel.

8. The apparatus recited in claim 1, wherein the element is a metal wire.

9. The apparatus recited in claim 1, wherein the element is a metal grid.

10. The apparatus recited in claim 1, wherein the element is a metal foil.

11. The apparatus recited in claim 1, wherein the reflector comprises an ellipsoidal reflector.

* * * * *

UNITED STATES PATENT AND TRADEMARK OFFICE
CERTIFICATE OF CORRECTION

PATENT NO. : 4,932,954
DATED : June 12, 1990
INVENTOR(S) : Fritz Wondrazek et al.

It is certified that error appears in the above-identified patent and that said Letters Patent is hereby corrected as shown below:

Change Column 3, line 32, to read

Figure 3:
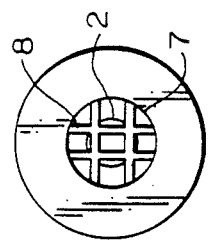
FIG. 3 shows the invention utilizing a metal grid element.

--e.g. grid or foil type elements, as shown in FIG. 3 (grid)--

Column 4, lines 20-21, claim 1, change

"...thereby fragmenting as solid body..." to read
--...thereby fragmenting the body...--

Column 4, line 29, claim 2, should read

--said laser energy guide means for providing a rinse fluid--

Signed and Sealed this

Fifth Day of May, 1992

Attest:

DOUGLAS B. COMER

*Attesting Officer*   *Acting Commissioner of Patents and Trademarks*